United States Patent [19]

Johnson

[11] 4,454,235
[45] Jun. 12, 1984

[54] CAPILLARY TUBE HOLDER FOR LIQUID TRANSFER IN IMMUNOASSAY

[75] Inventor: Leighton C. Johnson, Edwardsburg, Mich.

[73] Assignee: Miles Laboratories, Inc., Elkhart, Ind.

[21] Appl. No.: 383,826

[22] Filed: Jun. 1, 1982

[51] Int. Cl.³ .................... G01N 33/54; G01N 33/52
[52] U.S. Cl. .................... 436/536; 422/100; 422/102; 422/104; 436/180; 436/807; 436/810
[58] Field of Search ................ 422/99, 100, 102, 104; 436/180, 536, 807, 810

[56] References Cited

U.S. PATENT DOCUMENTS

| | | | |
|---|---|---|---|
| 3,525,264 | 8/1970 | Nieglos | 422/104 |
| 3,992,150 | 11/1976 | Retzer | 436/164 |
| 4,116,638 | 9/1978 | Kenoff | 424/104 X |
| 4,214,874 | 7/1980 | White | 422/100 X |

FOREIGN PATENT DOCUMENTS 2721942 11/1978 Fed. Rep. of Germany .

Primary Examiner—Sidney Marantz
Attorney, Agent, or Firm—Roger N. Coe

[57] ABSTRACT

An apparatus and method for transferring fluids (48) in a multi-liquid reagent protocol. Serum/plasma for a therapeutic drug assay is first obtained and mixed with a fluorogenic drug reagent (48) within a first cuvette (38). After mixing, the reaction product is accessed through a small opening (50) by tipping the cuvette (38). Fluid transfer is effected through a capillary tube (12) having an accurately calibrated bore (14), the capillary tube (12) being held between its open distal and proximal ends (30, 32) by a gripping sleeve (24). The capillary tube holder (10) is then inserted into a second cuvette where it suspends the capillary tube (12) over the liquid level (54) of a second reagent (56) in second cuvette (40). By vigorous up-and-down shaking of the second cuvette (40), the contents of the capillary tube (12) are discharged substantially uniformly throughout the liquid second reagent (56) in a short time period. Assay results are then obtained by inserting the second cuvette (40) and the reaction product of the second reagent within a fluorometer (60).

10 Claims, 10 Drawing Figures

B

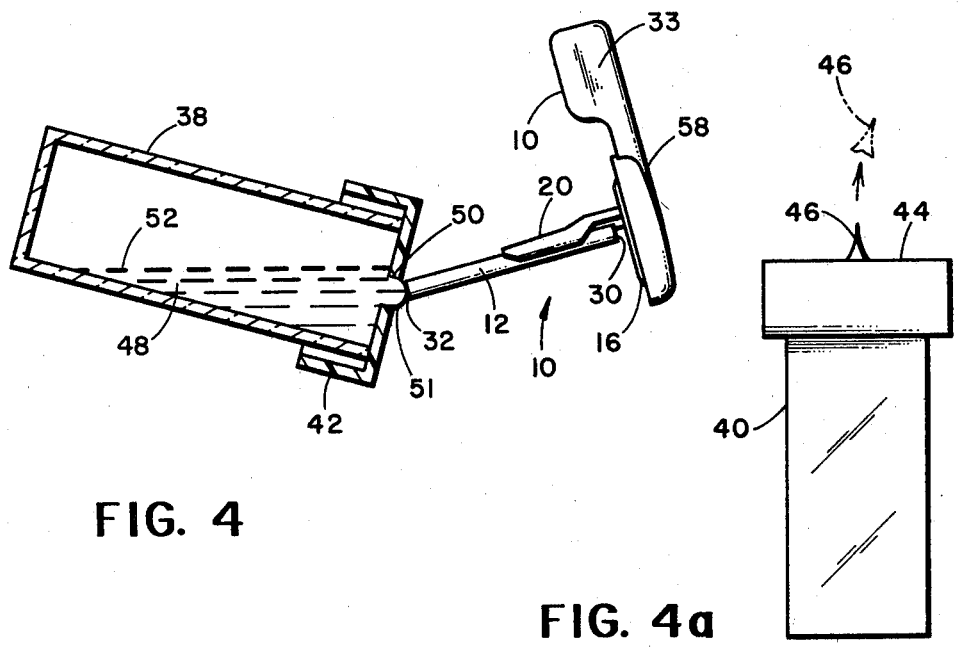
FIG. 4
FIG. 4a
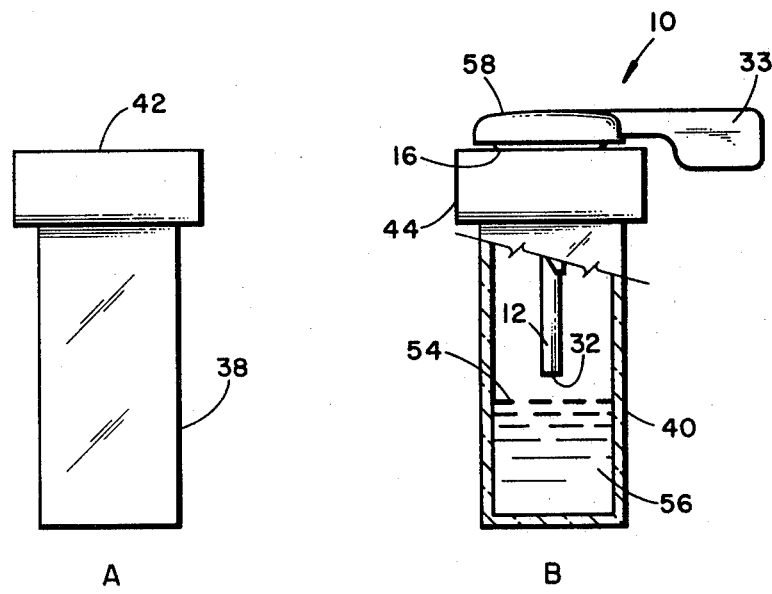
FIG. 5a
FIG. 5b

CAPILLARY TUBE HOLDER FOR LIQUID TRANSFER IN IMMUNOASSAY

FIELD OF THE INVENTION

This invention relates to assay methods and particularly to precisely measured fluid transfer and mixing, in a two-fluid reagent assay. The device used for effecting the fluid transfer is a capillary tube holder and capillary tube which transfers precisely measured reaction product from one liquid reagent container to a second container with a second reagent, and therein mixing the contents of the capillary tube with the second reagent within a definite critical mixing period.

DESCRIPTION OF THE PRIOR ART

The strategy of utilizing liquid reagents in performing assays in a nonradioisotopic procedure is set forth in detail in now issued U.S. Pat. No. 4,279,992 issued July 21, 1981, titled "Specific Binding Assay Employing An Enzyme-Cleavable Substrate As Label," Boguslaski, et al, assigned to the same assignee as the present application.

The use of a two-liquid reagent method in which the first reagent is reacted with blood serum/plasma and the reaction product then transferred to a second reagent for further reaction, the resulting product then being analyzed for a given ligand by a fluorometer is not new, and is known to the art. The two separate reagents are equally known, the first reagent being fluorogenic, the contents of the second reagent being generically known as an antibody. It should be understood that the composition of the two reagents and the procedure for use of two such independent reagents is not part of the present invention, but the immunoassay method so described, is improved by the present invention.

The blood sample securement and method of preparing the liquid sample for testing is disclosed in U.S. Pat. No. 4,104,025 issued Aug. 1, 1978, titled "Method of Preparing Liquid Samples for Testing" by Erich Retzer and assigned to Compur-Werk Gesellschaft mit beschraenkter Haftung & Co.

A one reagent mixture method is illustrated in U.S. Pat. No. 3,992,150 issued Nov. 16, 1976 and titled "Method and Equipment for Speedy Preparation of Test Liquids" by Erich Retzer and assigned to the same assignee as U.S. Pat. No. 4,104,025.

SUMMARY OF THE INVENTION

The improved procedures of the present invention lie in the methods for transferring fluid consisting of the reaction product of a first reagent and patient specimen e.g. serum or plasma, to the container of a second reagent and then thoroughly mixing an accurately measured amount of such reaction product with the second reagent, all of which is carried out within the limits of a narrowly defined time span and by means of a unique capillary tube and capillary tube holder device.

It has been found in the immunoassay protocol described, that the accuracy of the assay depends upon the transfer in a defined manner of a precisely measured amount of reaction product of patient specimen and fluorogenic drug reagent in the first container, to a second container which contains antibody reagent. This is accomplished by using an accurately calibrated bore of a precisely measured length of capillary tube held so that its free ends are at no time in contact with any other body. The capillary tube is filled by inserting only the tip of the capillary into a small globule of product which appears through a small orifice of the first container when the container or cuvette is tipped, bringing the small orifice below the liquid level in the first container. After the capillary tube is filled by capillary action, the capillary tube and its holder are then transferred to the container for the second reagent. The capillary tube is inserted into the second cuvette through an access opening which is then sealed by the undersurface of the capillary tube holder. The capillary tube is held in a suspended position over the level of the liquid reagent. The capillary tube is suspended by means of a standard which projects perpendicularly from the base and is integrally related to the base. A sleeve at the distal end of the standard has a narrow slit which provides a friction fit with the capillary tube. The sleeve grips the capillary tube at a location intermediate the capillary tube open ends. The contents of the capillary tube are then homogeneously mixed with the liquid second reagent by vigorously agitating the container in an up-and-down manner causing discharge of the capillary tube contents simultaneously with the second reagent washing over both open ends of the capillary tube which were heretofore suspended above the liquid level. Both the capillary tube discharge and the mixing occur within a narrowly defined time limit with the result that the capillary tube content is uniformly dispersed through the second reagent before their interaction is complete. Thereafter the second container together with the second reagent reaction product are fitted into a fluorometer and the assay results provided in either printed or display alphanumeric form.

BRIEF DESCRIPTION OF THE DRAWING

FIG. 4 illustrates filling the capillary tube by capillary action using a capillary tube holder and with the distal end of the capillary tube inserted into the globule.

FIG. 4a illustrates a second cuvette with a second liquid reagent and sealing spike in the cover of the cuvette.

FIG. 5a illustrates the first cuvette ("A") and FIG. 5b is the second cuvette ("B") and a capillary tube suspended within the second cuvette ("B") above the liquid level of the second reagent;

DESCRIPTION OF THE PREFERRED EMBODIMENTS

Figure 1:
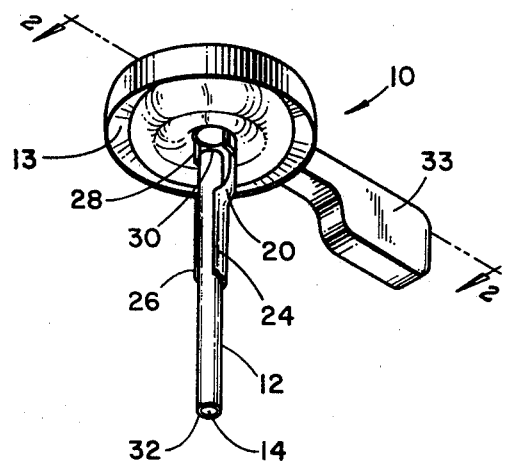
FIG. 1 is an isometric view of a capillary tube holder and associated capillary tube mounted therein.

Liquid transfer in the present invention, between the two liquid reagent containers, is illustrated in FIGS. 1-4. The transfer is by means of a capillary tube holder designated generally by reference numeral 10 and a capillary tube 12 which has an accurately calibrated bore 14 and is of a precise measured length in order to transfer an accurately defined volume of liquid which fills the capillary tube 12 by capillary action.

The plastic composition holder for the capillary tube 12 consists of a base 13 and integrally related handle 33 with the base 13 having a recess 15 (FIG. 2) and a sealing washer 16 press fitted with the recess 15 and permanently held therein.

Figure 2:
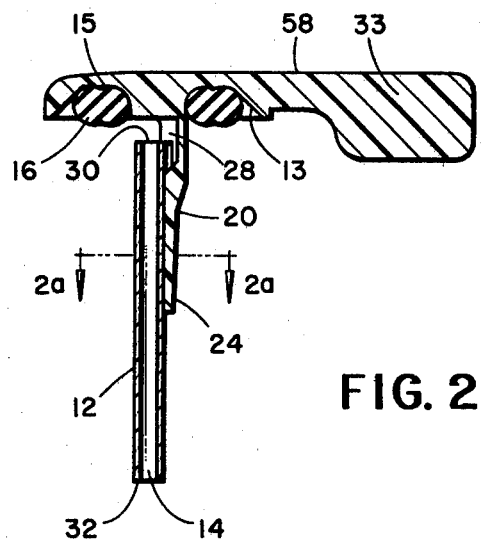
FIG. 2 is a section view taken on line 2—2 of FIG. 1.
Figure 2A:
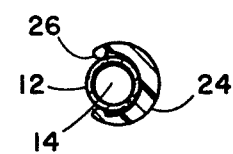
FIG. 2a is a section detail view taken on line 2a—2a of FIG. 2.

There projects from the undersurface of the base 13, a standard 20 terminating in a sleeve 24 with a longitudinal slit 26 enabling a friction fit with capillary tube 12 (FIG. 2a). Sleeve 24 encircles the major portion of the capillary tube 12 when the capillary tube is snap fitted in place. A marker 28 on the standard 20 defines the position for the proximal end 30 of the capillary tube so that the proximal end 30 and distal end 32 are accurately defined in position relative to the holder 10 and are further held so that the two open ends 30, 32 are unengaged by either the holder 10, or by any other structure during fluid transfer and mixing procedures.

While the composition of the plastic material composing the holder 10 can vary, of course, with design preference, typically the base 13, integrally related handle 33 and standard 20 consist of Delrin. The washer 16, while similarly selectable, as a matter of design preference may typically consist of about a 70 durometer urethane material. Mention of these two compositions is only by way of illustration and is not intended to be a limitation of the invention.

It is anticipated that the capillary tube holder can be made by any conventional means such as insert molding or the like.

Therapeutic Drug Assay Method

The immunoassay procedure contemplates two cuvettes, 38 and 40 (FIGS. 5a and 5b) also labeled "A" (cuvette 38) and "B" (cuvette 40). Cuvette 38 may if preferred have indented sides although not shown as such in FIGS. 3, 4, and 5. The purpose of having two differently shaped cuvettes is to maintain them readily distinguishable as can also be done by color coding the sealing covers 42 and 44.

Figure 3:
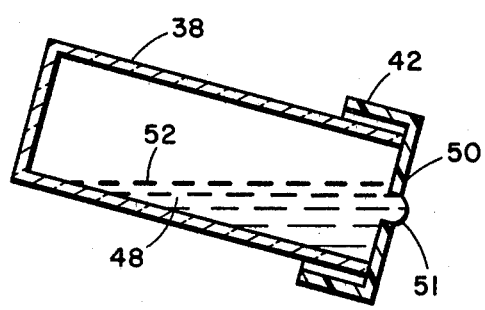
FIG. 3 illustrates a cuvette containing a liquid reagent first reacted with serum/plasma and then tipped so that a small globule is formed below fluid level and projecting through the access opening.

Each cuvette cover has a spike 46 which normally seals an access opening in the cover. The spike is not broken off until the appropriate stage of the assay (FIG. 4a). It should be noted that the spike has already been broken away in cuvette 38 (FIGS. 3, 4 and 5). Cuvette 38 contains a fluorogenic drug reagent which is in liquid form and designated by reference numeral 48.

In the therapeutic drug assay procedure, blood is first obtained from the donor, i.e., the patient whose assay is in question. The procedure is outlined in U.S. Pat. No. 3,992,150 (supra). The blood sample is centrifuged in a known manner which separates the serum/plasma from the blood cells and the serum/plasma received in a capillary (not shown) which is dropped through access opening 50 of cover 42 on cuvette 38 and into the fluorogenic drug reagent 48. The serum/plasma and reagent 48 are thoroughly mixed after putting an adhesive seal over opening 50 to retain the contents of cuvette 38 during mixing.

The reaction product from cuvette 38 is then transferred to cuvette 40 by means of the capillary tube holder 10 and capillary tube 12 (FIG. 4). By tipping the cuvette 38 in the manner shown in FIGS. 3 and 4 the access opening 50 is brought below fluid level 52. The dimension of the access opening 50 is sufficiently small so that liquid will not "pour" through the opening, instead there will be generated a globule 51 of fluid extending at least partially through the access opening 50. The very tip distal end of capillary tube 12 is carefully applied against the globule 51 of extending fluid, all of which occurs without touching the edges of the opening 50 or any other portion of the cover 42.

By capillary action, the capillary tube is filled from distal end 32 to proximal end 30. Since the bore 14 is accurately calibrated and the length of the capillary tube accurately measured, a precise quantity of the reaction product is obtained.

Next the spike 46 on cover 44 of cuvette 40 is broken away and distal end 32 of the capillary tube is carefully inserted through the access opening again without touching either the side of the opening or the inner walls of cuvette 40. Note from FIG. 5b that the end 32 of the capillary tube is suspended above the liquid level 54 of the second reagent 56. The composition of the reagent 56 is not part of the present invention but for illustration purposes the composition may be an antibody.

Figure 6:
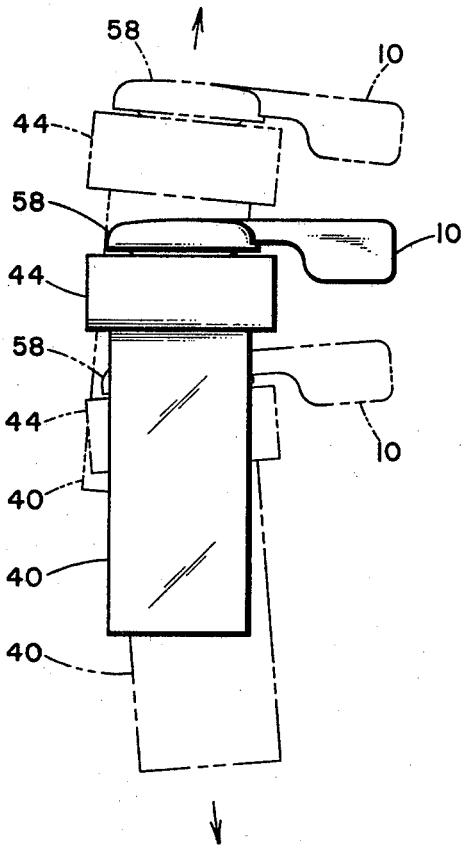
FIG. 6 illustrates the mixing step wherein the contents of the capillary tube in FIG. 5b are mixed with the liquid reagent of cuvette ("B") to produce a reaction product which is then measured by a therapeutic drug assay utilizing a fluorescence intensity measuring device; and, FIG. 7 illustrates in schematic form a top view of a fluorometer.

It has been found that the contents of capillary tube 12 must be thoroughly and rapidly mixed with reagent 56 in order for the reaction product to lend itself to an accurate fluorometric analysis. It has been found that the reaction which occurs between the contents of the capillary tube 12 (FIG. 5b) and second reagent 56 depends for accuracy and precision on a complete distribution of the contents of capillary tube 12 with all portions of the reagent 56 while the reaction proceeds to completion. A critical factor, therefore, is the speed with which the mixing can occur and this depends upon the discharge rate of the capillary tube 12 and the rate at which the capillary tube contents can be dispersed through the reagent 56. Typically, this must occur within approximately 1 to 5 seconds which is the critical time period for mixing-and-reacting of the contents of capillary tube 12 and the second liquid reagent 56. This is accomplished by means of finger pressing the upper surface 58 of the base 13 toward the access opening in cover 44 for cuvette 40 while at the same time vigorously shaking the cuvette 40 in an up-down vertical movement in the manner illustrated in FIG. 6. The washer 16 seals the opening in cover 44 of cuvette 40, formed when spike 46 (FIG. 4a) is broken away. This confines the liquid within the cuvette interior, while the cuvette is shaken up and down.

In some not thoroughly understood manner, but which may perhaps consist of slugs of fluid successively leaving and entering the capillary tube 12, a thorough mixing of the capillary tube contents occurs within a short period of time throughout the body of the liquid reagent 56, i.e., within a time period of about 1 to 5 seconds. The contents of the capillary tube 12 thoroughly and homogeneously disperse within reagent 56 and the two liquids are reacted.

Figure 7:
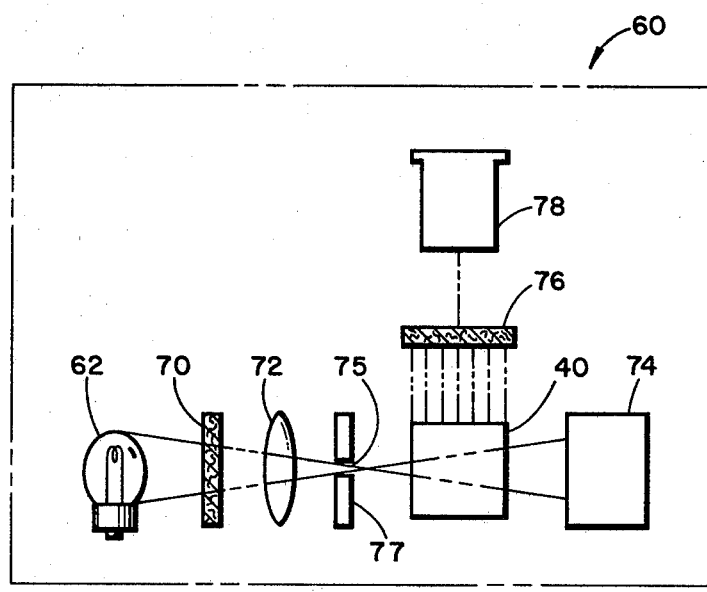

The reaction product obtained, in the manner so described, together with the cuvette 40 is next mounted within a fluorometer designated generally by reference numeral 60 (FIG. 7) where a light source 62 produces light passed through filter 70, lens 72 and aperture 75 of shutter 77. After passing through cuvette 40, the remaining light energy is trapped by a light trap 74 which limits the diffusion of light essentially to the path described. The chromophores within the cuvette 40 emit at 450 nanometers and light from source 62 emits at 405 nanometers. The luminescence from the chromophores in cuvette 40 is directed transversely to the path of light developed from light source 62. The luminescence is filtered through a filter 76 and then to a photomultiplier 78. The light intensity is transduced to an electrical signal output with a value correlated to the luminescence intensity, hence directly related to the ligand in cuvette 40.

The present invention is further useful in that this scheme of light analysis is unimpeded by the presence of a capillary tube, i.e., in prior practice when transferring fluid from cuvette 38 to cuvette 40 the calibrated capillary tube was simply dropped into cuvette 40 and unless displaced out of a light impeding position would interfere with the accuracy of the assay. Such problem is wholly obviated in the present invention for reasons described. The intensity of fluorescent light processed as described is transduced into a voltage which is "read" either as a printed value or an alphanumerical display. The readout provides a measure of drug concentration in the blood, thus enabling a more accurate prescription of amount of drug which should be administered to obtain the acceptable or preferred level of drug concentration in the blood of a patient.

The procedure described is readily applicable for therapeutic drug assay in a wide spectrum of drugs which includes, but is not limited to, assays for Gentamicin, Sisomicin, Netilmicin, Tobramycin, Kanamycin, Amikacin, Diphenylhydantoin, Phenobarbital, Theophylline, Carbamazepine, Primodone, Quindine and others.

Conclusions

The described capillary tube, and capillary tube holder, represent a cost effective, accurate and precise transfer method between the two liquid reagents in a two-liquid reagent immunoassay method employing fluorescence intensity as the parameter in a method of assaying therapeutic drugs in a patient's blood stream. The described method enables virtually instantaneous mixing of the fluorogenic drug reagent-and-serum with antibody reagent in a second cuvette. Because the capillary tubes, cuvettes and capillary tube holder are disposable, there is no required maintenance, and no unkeep. Moreover, the capillary tubes do not require calibration and form an accurate and precise method for dispensing fluids in an accurate manner. Since the volumes transferred are small, change in temperature of the materials in the cuvettes is minimal and acceptable.

Claim Scope

While the present invention has been illustrated and described in connection with a selected example embodiment, it will be understood that this is illustrative of the invention and is by no means restrictive thereof. It is reasonably to be concluded that those skilled in the art can make numerous revisions and adaptations of the invention and it is intended that such revisions and adaptations will be included within the scope of the following claims as equivalents of the invention.

What is claimed is:

1. In a method for determining a ligand in a liquid medium, formed by combining blood serum/plasma with a fluorogenic reagent, the steps comprising:

thoroughly mixing the blood serum/plasma with the fluorogenic reagent, transferring a sample of the resulting reaction product to a second reagent through an accurately calibrated bore of a capillary tube suspended by a capillary tube carrier between its ends by means of a standard projecting from the undersurface of the carrier, positioning the suspended capillary tube within a container for the second reagent and above the liquid level of the second reagent, sealing an access opening of the container of the second reagent by pressing the undersurface of the capillary tube carrier about the periphery of the access opening;

and thereafter uniformly dispersing the contents of the capillary tube throughout the second reagent and within a relatively short time period, by agitating the liquid-second-reagent container and capillary-holder while maintaining the ends of the capillary tube open and accessible to the liquid second reagent during mixing.

2. The method in accordance with claim 1 wherein pressure is constantly applied between the undersurface of the capillary tube carrier and the container for the second reagent to prevent egress of the fluid through the access opening which is sealed by the undersurface during agitation of the second reagent container.

3. The method of claim 2, including a step of measuring fluorescence intensity of the reaction product of the capillary tube contents and said second liquid reagent by means of a fluorometer.

4. In a method for therapeutic drug assay in which blood serum/plasma is first introduced to a first reagent within a cuvette, the steps comprising:

supporting a capillary tube between its ends by a capillary tube holder comprised of a base, and a standard projecting perpendicularly from the undersurface of the base and to which the capillary is coupled with the open ends of the capillary open and at all times unengaged, transferring a sample of the thoroughly mixed resulting reaction product of serum/plasma and first reagent within the cuvette by filling the accurately calibrated bore of said capillary tube by the force of capillary action with a portion of such reaction product, thereafter transferring the filled capillary tube and capillary tube holder to a second reagent in a separate cuvette and with the capillary tube and capillary tube contents suspended over the liquid surface of the second reagent and with the access opening of the second cuvette sealed by the undersurface of said capillary tube holder, and uniformly mixing the contents of the capillary tube bore with the second reagent by agitating the second cuvette to discharge the capillary tube contents substantially uniformly throughout the volume of the second reagent and within a critical predetermined time.

5. The method of claim 4, including the step of applying pressure to the external surface of the capillary tube holder base to maintain the base in sealing relation with the access opening whereby none of the contents of the second cuvette is lost during the mixing step.

6. A capillary tube holder comprising a base, having a recess at the undersurface thereof, annular sealing means received within said recess, a standard projecting substantially transversely to the base and integrally joined with the undersurface of the base, a sleeve formed at the projected end of the standard and having a slit formed lengthwise of the sleeve whereby a capillary tube can be force fitted into said sleeve at a mid portion of the capillary tube whereby the two opposite ends of the capillary tube are unengaged by any of the capillary tube holder structure.

7. The capillary tube holder according to claim 6, including a marker means formed on said standard to illustrate the operative position for the open capillary end adjacent the base undersurface.

8. The capillary tube holder in accordance with claim 7 including means integrally formed with the base and extending beyond the periphery of the base to provide a gripping and holding handle for the capillary tube holder.

9. The capillary tube holder of claim 6 comprised of a one-piece molded plastic material consisting of Delrin and in which the sealing means is a relatively soft construction consisting of polyurethane material.

10. A method for fluid transfer and mixing in a therapeutic drug assay procedure comprising the steps of:
   suspending a capillary tube filled with a portion of reaction product of a liquid fluorogenic reagent and blood serum, over the upper surface of antibody and with opposite open ends of the capillary tube unobstructed and uncontacted,
   and, rapidly shaking the container of antibody to agitate the antibody and thoroughly disperse the contents of the capillary tube in the antibody and within a predetermined critical time period.

* * * * *